United States Patent [19]
Amsden et al.

[11] Patent Number: 5,302,397
[45] Date of Patent: Apr. 12, 1994

[54] POLYMER-BASED DRUG DELIVERY SYSTEM

[76] Inventors: Brian G. Amsden, 40 Fountainhead Rd., Apt. #1516, Downsview, Ontario M3J 2V1; Yu-Ling Cheng, 1399 Glenburnie Rd., Mississauga Ontario L5G 3C7, both of Canada

[21] Appl. No.: 793,836

[22] Filed: Nov. 19, 1991

[51] Int. Cl.$^5$ .............................................. A61K 9/26
[52] U.S. Cl. .................... 424/473; 424/426; 424/469; 424/486
[58] Field of Search ................ 424/469, 473, 426, 486

[56] References Cited

U.S. PATENT DOCUMENTS

| | | | |
|---|---|---|---|
| 4,177,256 | 12/1979 | Michaels et al. | 424/22 |
| 4,391,797 | 7/1983 | Folkman et al. | 424/19 |
| 4,478,818 | 10/1984 | Shell et al. | 424/426 |
| 4,684,524 | 8/1987 | Eckenhoff et al. | 424/473 |
| 4,692,336 | 9/1987 | Eckenhoff et al. | 424/469 |
| 4,693,895 | 9/1987 | Wong et al. | 424/473 |
| 4,777,049 | 10/1988 | Magruder et al. | 424/457 |
| 4,783,337 | 11/1988 | Wong et al. | 424/468 |
| 4,795,436 | 1/1989 | Robinson | 424/426 |
| 4,981,841 | 1/1991 | Gibson | 514/2 |
| 4,997,652 | 3/1992 | Wong | 424/428 |

FOREIGN PATENT DOCUMENTS

| | | |
|---|---|---|
| 0140998 | 5/1985 | European Pat. Off. |
| 0417572A2 | 3/1991 | European Pat. Off. |
| 2215614A | 9/1989 | United Kingdom |
| WO89/05656 | 6/1989 | World Int. Prop. O. |

OTHER PUBLICATIONS

Theeuwes et al. (Dec. 1975) The Journal of Pharmaceutical Sciences 64:1987-1991, describes the elementary osmotic pump.
Gale et al. (1980) Journal of Membrane Science 7:319-331, describes the use of osmotically active therapeutic agents in monolithic systems.
Wright et al. (1981) AIChE Symposium Series 77:62-68, describes a model for the release of osmotically active agents from monolithic polymeric matrices.
Carelli et al. (1988) Int. Journal of Pharmaceutics 50:181-188, describes drug release from silicone elastomer through controlled polymer cracking: an extension to macromolecular drugs.
Golomb et al. (1990) Journal of Controlled Release 12:121-132, describes the relationship between drug release rate, particle size and swelling of silicone matrices.
Di Colo (1991) Proceed. Intern. Symp. Control. Rel. Bioact. Mater. 18:317-318, describes controlled drug release from implantable matrices based on hydrophobic polymers.
McClelland et al. (1991) Pharmaceutical Research 8:88-92, describes the solubility-modulated osmotic pump: in vitro/in vivo release of diltiazem hydrochloride.
Onggowarsito et al. (1991) Proceed. Intern. Symp. Control. Rel. Bioact. Mater., 18:227-228, describes the release of drugs having pH-dependent solubility from an osmotic delivery device.

*Primary Examiner*—Thurman K. Page
*Assistant Examiner*—Amy Hulina
*Attorney, Agent, or Firm*—Foley & Lardner

[57] ABSTRACT

Described herein is a drug delivery system useful to deliver drugs at low dosage levels to patients in a sustained fashion and at a controlled rate. The system comprises a wettable polymeric matrix in which is dispersed a multiplicity of particles containing a substantially homogeneous blend of osmotically active excipient and not more than about 10% by weight of drug. The system is particularly well suited for delivery of therapeutic macromolecules such as protein drugs. Delivery of epidermal growth factor is exemplified.

19 Claims, 3 Drawing Sheets

POLYMER-BASED DRUG DELIVERY SYSTEM

FIELD OF THE INVENTION

This invention relates to drug delivery systems. More particularly, the invention relates to the use of polymer-based vehicles useful for delivering therapeutic agents including protein drugs such as epidermal growth factor, particularly at controlled and relatively low dose release rates.

BACKGROUND TO THE INVENTION

Conventional drug administration methods entail periodic dosing of a therapeutic agent in a formulation that ensures drug stability, activity, and bioavailability. These methods of administration include parenteral delivery such as by injection, topical delivery using salves or ointments for skin applications or via liquid drops for eye and ear applications, and oral delivery by ingestion, for example of pills, tablets or liquids. Administration of these drug dosage forms results typically in a sharp initial increase in drug concentration, followed by a steady decline in concentration as the drug is cleared and/or metabolised. Repeated administration is necessary, to reach and maintain the drug concentration within the appropriate efficacy range. The result of this periodic drug delivery is a drug concentration profile that oscillates over time.

For drugs that are unstable in the blood stream or gastrointestinal tract, are toxic at high doses or have a narrow therapeutically effective concentration range (therapeutic window), conventional drug delivery methods are inappropriate. Recently developed protein drugs, for example, present unique challenges for drug delivery. Because of their protein nature, oral administration results in protein digestion or hydrolysis in the gastrointestinal tract. Proteins also have very short pharmacokinetic half-lives in the blood stream, being quickly metabolized and cleared, which renders parenteral administration inappropriate. Also, because of their size, proteins are poorly absorbed through the skin and so cannot readily be delivered by topical administration.

To provide for the delivery of such macromolecular drugs, and particularly protein drugs, alternatives to the traditional delivery methods have been explored. One promising approach entails the use of biocompatible, non-degradable polymers as drug delivery vehicle. In this approach, the drug is dispersed within a polymeric matrix that is wettable, i.e., capable of imbibing water, and which serves to control the rate at which drug is released. Use of these polymeric delivery vehicles offers several advantages over conventional modes of drug administration. Polymeric systems can be localized to the desired target site, for example by topical application, by implantation, or by ingestion, to reduce systemic toxicity and increase drug potency. Because of the controlled rate at which these polymeric vehicles release drug, plasma drug concentrations can be maintained within an appropriate therapeutic window, and harmful side effects reduced. Also, the discomfort associated with multiple injection therapy can be eliminated, thus improving patient compliance.

A variety of polymer-based drug delivery systems have been developed, which differ largely in the mechanism by which release of the drug from the matrix is achieved. For low molecular weight drugs that are soluble in polymer, for example, release from the matrix can occur by diffusion, with the drug dissolving in water imbibed by the matrix and then diffusing down the chemical gradient to the polymer surface. Release by dissolution/diffusion has been demonstrated in polymers such as silicone rubber, polyethylene and nylon film, for such drugs as testosterone, phenobarbital, progesterone and caffeine.

The large size of macromolecular compounds, such as peptide and protein drugs, was thought to be prohibitive to diffusion from the polymeric matrix. Prolonged release of proteins in the size range from 14 kD to 250 kD was achieved, but at poorly controlled rates, by loading into a matrix of polyethylene-vinyl acetate (EVA), polyhydroxyethyl methacrylate or polyvinylalcohol (see Langer et al, Nature, 1976, 263:797; and see Langer et al, U.S. Pat. No. 4,391,797 issued Jul. 5, 1983). Studies of the protein release kinetics indicated that proteins were released from the matrix by first dissolving in matrix-imbibed water, leaving voids in the matrix which when invaded by water caused the dissolution of neighbouring protein molecules, thereby creating a network of pores leading to the matrix surface. Prolonged release appeared therefore to arise from the tortuous paths generated by the dissolution/diffusion process.

A drawback of delivery devices that employ a diffusion-based release mechanism is that drug release is time-dependent, that is, a constant amount of drug is not delivered over the life of the device. As with conventional modes of drug administration, drug release follows first order kinetics, and an initial sharp increase in drug concentration is followed by a drug concentration that declines gradually as the matrix-loaded drug dissolves. Moreover, the porous network required for diffusional release of the drug to the external environment can be established only by high volumetric loading of drug in the matrix, which raises concerns for toxicity and adverse side effects, and is particularly inappropriate for proteins and other drugs that require low dosages, and have a narrow therapeutic window, i.e., the difference between the lethal dose ($LD_{50}$) and the effective dose ($ED_{50}$) of a given drug.

An alternative to the mechanism of drug release by diffusion from polymers, and one which offers drug release at a prolonged and constant rate, is that of osmotic rupturing, which relies on osmotic pressure as the driving force for drug release. In this approach, osmotically active drugs or drug salts are dispersed as discrete particles within a wettable, polymeric matrix, typically polyethylene-vinyl acetate copolymer or polydimethylsiloxane. In response to water imbibed by the matrix, particles encapsulated therein swell as osmotic pressure builds until the tensile strength of the elastomer is overcome, and eventually ruptures, releasing the drug particles which further dissolve in the aqueous environment. Serial rupturing in this manner generates a porous network, allowing water to migrate further within the matrix, thereby causing further rupturing and drug particle release.

Drug delivery systems employing the osmotic rupturing mechanism of drug release are particularly attractive because they offer sustained and relatively constant drug release profiles. However, as with systems based on the diffusion mechanism of drug release, the osmotic rupturing mechanism requires relatively high volumetric loading of the polymer, to establish the porous network required to sustain rupturing and drug release. This makes low dose delivery of drugs problematic when osmotic rupturing type delivery devices are contemplated.

It is an object of the present invention to provide a polymer-based delivery system which is adapted to release a selected drug in low dose levels and in a sustained and controlled release fashion.

It is another object of the present invention to provide a polymer-based delivery system which is adapted for use generically to release a therapeutic macromolecule at low dose levels and in a sustained and controlled release fashion.

It is another object of the present invention to provide a method for delivering a therapeutic macromolecule to a patient in low dose levels at a sustained and relatively constant rate.

It is another object of the present invention to provide a process for preparing a polymer-based system which is useful to release a selected therapeutic macromolecule in low dose levels at a sustained and relatively constant rate.

SUMMARY OF THE INVENTION

The present invention provides a polymer-based delivery system of novel design, which is structured to provide sustained and rate-controlled release of therapeutic agents, including particularly macromolecular therapeutic agents such as protein drugs. In the present delivery system, the drug is dispersed within a polymeric matrix in the form of particles that contain a preponderance of osmotically active excipient and only a small fraction by weight of the desired drug. By incorporating in the particle a weight fraction of drug that is appropriately small relative to osmotic excipient, the drug is released at a rate that is dictated predictably by the osmosity of the excipient used for particle formation. In addition, by controlling the volumetric loading of polymer by the drug-containing excipient particle, and particle size distribution, the amount of drug released over time can also be controlled, in accordance with the present invention.

According to one aspect of the present invention, there is provided a drug delivery system useful for delivering a drug at low dosage levels to a patient in a sustained and controlled release fashion, the system comprising a matrix formed of a wettable polymer and, dispersed uniformly within the polymer, a multiplicity of particles each comprising a substantially homogeneous blend of drug and osmotically active excipient, wherein the amount of drug in each of said particles is insufficient to alter significantly the osmosity of the osmotically active excipient therein. Put another way, the desired weight ratio of drug:excipient in the particle is less than or equal to the ratio of solubilities of drug:excipient, in a saturated salt concentration.

In a particular aspect of the invention, there is provided a drug delivery system useful for delivering therapeutic amounts of a drug to a patient in a sustained and controlled release fashion, the system comprising a matrix formed of a wettable polymer and, dispersed uniformly within the polymer, a multiplicity of particles each containing a substantially homogeneous blend of drug and sodium chloride, wherein the amount of drug contained in each of said particles is not greater than about 10% of the particle, by weight.

According to another aspect of the present invention, there is provided a method for delivering a selected drug to a patient, which comprises the step of administering to said patient a drug delivery system of the present invention.

According to an embodiment of the present invention, the drug-containing polymer so produced is shaped for delivery to the patient either by implantation, by topical delivery or by ingestion.

According to another aspect of the present invention, there is provided a process for preparing a drug delivery system useful to deliver a drug at low dosage levels to a patient in sustained and controlled release fashion, comprising the steps of obtaining particles comprising a substantially homogeneous blend of osmotically active excipient and drug, wherein the drug component of the particles is not more than about 10% by weight, and then dispersing said particles uniformly in a wettable polymeric matrix.

In accordance with another aspect of the invention, there is provided a substantially homogeneous assemblage of particles which when dispersed in a wettable polymeric matrix are useful to deliver a drug in low dosage levels to a patient in a sustained and controlled fashion, said particles comprising a substantially homogeneous blend of osmotically active excipient and drug, wherein the drug component of the particles is not more than about 10% by weight.

These and other aspects of the present invention are now described in greater detail with reference to the accompanying drawings, in which:

DETAILED DESCRIPTION OF THE INVENTION AND PREFERRED EMBODIMENTS

Figure 1A:
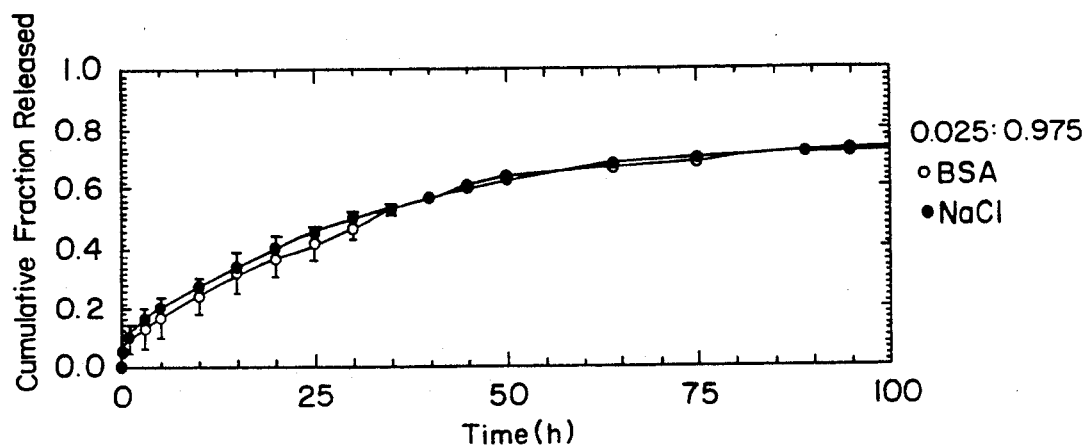
FIGS. 1(A)–(D) illustrate the release profile of bovine serum albumin from a polymeric matrix at various volumetric loadings.
Figure 1B:
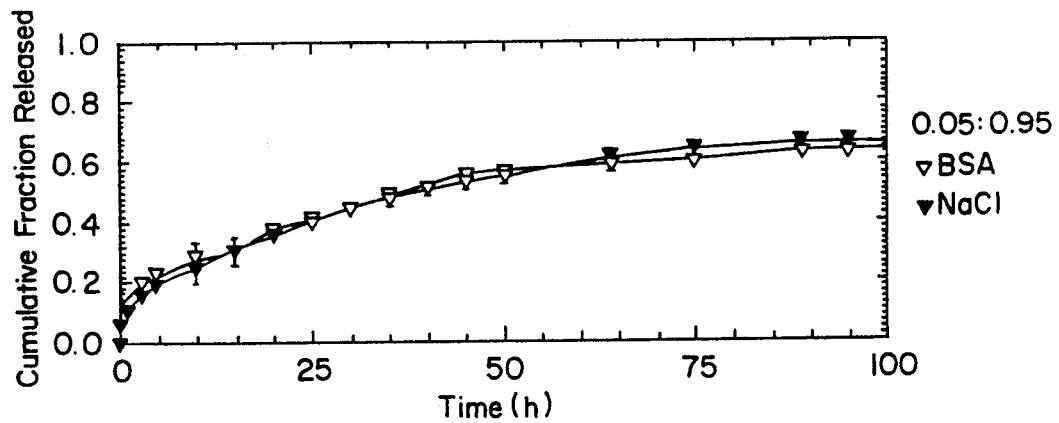
Figure 1C:
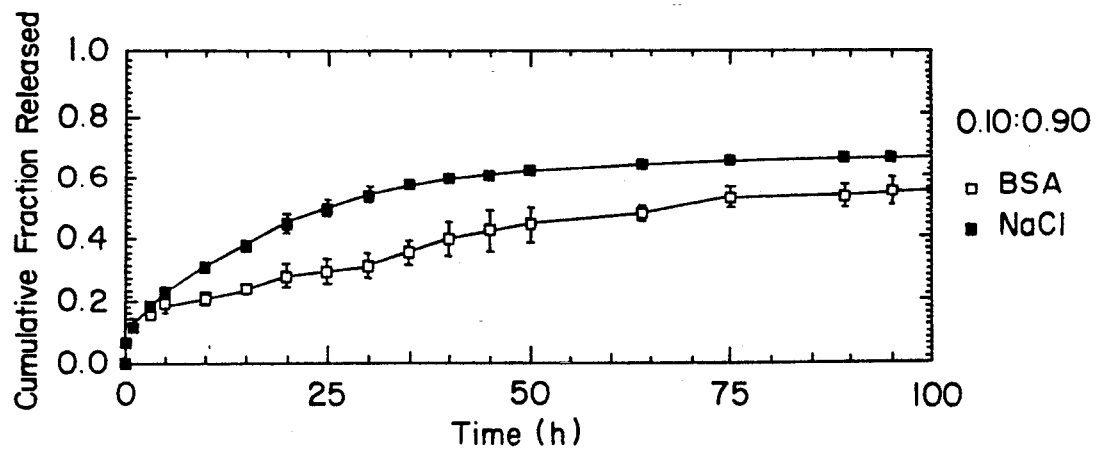
Figure 1D:
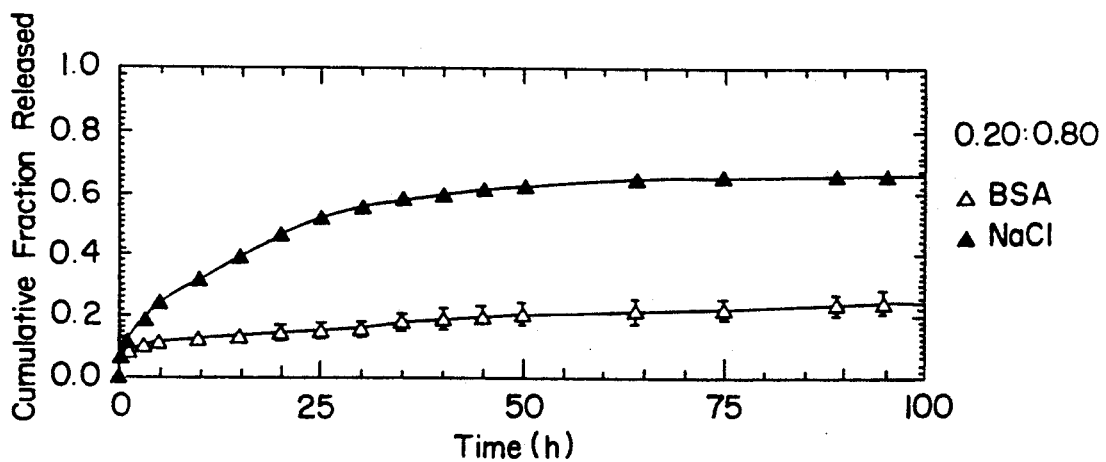

The present invention provides a drug delivery system adapted to release, primarily by osmotic rupturing, relatively low dose levels of drugs and especially therapeutic macromolecules, in a sustained and controlled release fashion. The present delivery devices are designed to strike a balance between the high volumetric loading required for drug release by diffusion from a porous matrix, and the low volumetric loading required for drug release at low dose levels. This is achieved by loading the polymeric matrix with particles containing a substantially homogeneous blend of drug and osmotically active excipient, wherein the amount of drug in each of the particles is not more than about 10% by weight of the particle. In this weight ratio, the drug-containing particles behave osmogenetically in virtually the same manner as excipient particles per se. This results in a drug release profile having the same zero order release kinetics as are common for osmotic excipient release profiles. Notably, however, because the drug is present at only low levels within the polymeric matrix, drug release is limited, at a predominantly constant rate, to low dose levels. In addition to these benefits, the present delivery devices release drug at a rate that is coordinated virtually precisely with the excipient release rate. The present delivery system thus provides a generic delivery system which permits the release rate of any particular drug delivered from the system to be reliably and generically predicted, simply from knowledge of the release profile of the osmotic excipient used in particle formation.

Polymers appropriate for use as matrix in the present delivery devices are biocompatible and generally resistant to chemical attack by the environment of use so that the matrix remains intact during the period of drug release. In addition, appropriate polymers are those capable of mediating the osmotic rupturing mechanism of drug release, and accordingly should be wettable, i.e. capable of imbibing water, and have a tensile strength allowing expansion and rupture in response to localized osmotic pressure. Suitable for use as polymeric matrix in the present delivery devices are the elastomers, such as ethylene-vinyl ester copolymers, including ethylene-vinyl acetate copolymer which is presently preferred herein. Acceptable properties are also exhibited by silicon-based elastomers, such as polydimethylsiloxane.

The types of drugs that can be delivered using the present delivery system are numerous, and include both small molecular weight compounds in the size range from 100 daltons to about 1,000 daltons as well as the larger macromolecular drugs, such as peptide and protein drugs in the size range from about 1,000 daltons to about 100,000 daltons, and beyond. The system is particularly well suited to deliver drugs having relatively low effective doses e.g. in the micrograms/day, nanograms/day and even picograms/day range.

Among the protein drugs which may be delivered using the present delivery system are: the peptide hormones such as insulin, glucagon, parathyroid hormone, calcitonin, vasopression, renin, prolactin, growth hormone, the gonadotropins including chorionic gonadotropin, follicle stimulating hormone, thyroid stimulating hormone and leutenizing hormone; physiologically active enzymes such as transferases, hydrolases, lyases, isomerases, phosphatases, glycosidases, superoxide dismutase, factor VIII, plasminogen activators; and other therapeutic agents including protein factors such as epidermal growth factor, insulin-like growth factor, tumour necrosis factor, transforming growth factors, fibroblast growth factors, patelet-derived growth factors, erythropoietin, colony stimulating factors, bone morphogenetic proteins, interleukins and interferons. Non-protein macromolecules, particularly including polysaccharides, nucleic acid polymers, and therapeutic secondary metabolites including plant products such as vinblastine, vincristine, taxol and the like may also be delivered using the present system. Small molecular weight compounds may also be administered as well, of course.

The osmotically active excipients useful for the purpose of this invention are soluble in aqueous and biological fluids, and include ionizable compounds, inorganic and organic acids, bases and especially salts. Most suitably, the compounds are solids at body temperature, and they dissolve and form a solution with fluids imbibed into the osmotic device. Electrolytes are particular suitable for use as osmotic excipients. Examples of inorganic salts useful as excipient in the present delivery system include magnesium chloride, magnesium sulfate, potassium chloride, potassium sulfate, potassium acid phosphate, sodium chloride, sodium sulfite, sodium sulfate, sodium nitrite, sodium nitrate, and the like. Salts of organic acids include sodium citrate, potassium tartrate, potassium bitartrate, and the like. Ionizable solid acids may also be employed as osmotic excipient, and these include for example, tartartic, citric, maleic, malic, fumaric, tartronic, itaconic, adipic, succinic, mesaconic, and the like. Basic compounds useful as excipient in the particles include potassium carbonate, sodium carbonate, ammonium carbonate and the like.

Excipients preferred for use in the present delivery system are the ionizable inorganic salts, including sodium chloride and potassium chloride, of which sodium chloride is particularly preferred.

For loading within the polymeric matrix, the present invention provides a substantially homogeneous assemblage of particles, each containing a substantially homogeneous blend of osmotic excipient and drug. The particles are prepared by first intimately mixing pre-selected amounts of the chosen excipient and drug. Mixing is performed most suitably by co-dissolving electrolyte and drug in water (minimal volume is preferred) with vigorous agitation, and then re-crystallizing the blended components by lyophilization. As an alternative to lyophilization, crystallization may be achieved by subjecting the dissolved drug/excipient mixture to extensive vacuum at room temperature, to evaporate water.

After the drug and excipient are blended, an assemblage of particles having a substantially homogeneous size distribution is generated, for dispersion in the polymeric matrix. The assemblage can be generated by various techniques. For example, once crystallized, the blended components are ground and optionally wet-sieved with warm petroleum ether, and then size-selected by sieving through mesh of appropriate size. Selection of particles having an appropriate size distribution is an important factor in constructing the present drug delivery system. Particle size distribution affects the rate at which drug is released from the polymeric matrix, in response to imbibed water. With larger particles, which accordingly contain greater amounts of drug, the drug will be released at relatively fewer intervals but in relatively larger amounts. Conversely, and assuming equivalent polymer loading, particles having a smaller size distribution will result in drug release at more frequent intervals but in relatively smaller amounts. Release is better sustained and more highly controlled using particles having a relatively smaller size distribution, e.g. in the range from about 104 $\mu$m to about 147 $\mu$m, or smaller. Particles having the desired size distribution are readily recovered by sieving the ground, crystalline blend of drug/excipient between two screens of appropriate mesh size, in accordance with standard techniques. It should be understood that particles having a different size distribution may also be employed, without sacrificing the predictability of drug release kinetics offered by the present delivery system. For certain applications, for instance to deliver low dose drugs having a therpeutic window near one of the extremes of the low dose range, a particle size distribution in the 147 $\mu$m-175 $\mu$m range (e.g. for ug/day delivery) range or in the 74 $\mu$m-104 $\mu$m range (e.g. for pg/day delivery) may be desirable, depending on the release kinetics desired for delivery of a particular drug.

It should be understood that the drug component of the particles may comprise two or more drugs in combination, if desired. For example, epidermal growth factor may be incorporated in wound healing combination with a non-steroidal anti-inflammatory agent, such as indomethacin. Similarly, epidermal growth factor, or transforming growth factor may be incorporated in wound healing combination with platelet-derived growth factor (see e.g. WO89/05656 published Jun. 29, 1989).

As noted above, the mixing of excipient and drug in amounts appropriate for sustained and controlled low dose release of drug is an important parameter. In general, determination of relative amounts appropriate for desired drug release kinetics will of course take into account the dose range at which the drug is effective, and is otherwise within the range between 0-10% by weight of the particle. Specific determinations of appropriate % weight of the drug component of the particle can be made readily in drug release experiments of the type herein exemplified. Once selected, the drug and excipient can be dissolved in the desired weight ratio, and the particles prepared as described hereinabove.

To prepare the delivery device, particles are dispersed within the selected polymer using a protocol that is dictated primarily by the choice of polymer. Once the particles are prepared and size-selected, they are dispersed uniformly within the selected polymer to achieve a volumetric loading which is appropriate for a porous network to form upon serial osmotic rupturing, and appropriate for the drug dosage level desired. For particles in the size range of 104-147 $\mu$m, volumetric loading of particles in the matrix is suitably in the range from about 10% to about 30%, more desirably from about 15% to 25%, and ideally about 20%, i.e., 19-21%. For particles having a larger size distribution e.g. 147-175 $\mu$m, lower volumetric loadings may be used, of around 10%-20%. Similarly, particles having a smaller size distribution e.g. 74-104 $\mu$m, can be loaded in the volumetric range from 20%-30%. In a preferred embodiment of the invention, the particles have a size distribution in the 104 $\mu$m to 147 $\mu$m range, and are dispersed uniformly in the matrix at around 20% volumetric loading.

To achieve appropriate volumetric loading, particles and polymer in either cured or uncured state are mixed simply in the desired volumetric ratio. To prepare matrices based on polydimethylsiloxane for example, dispersion is achieved while the polymer is in the uncured state. In particular, particles are mixed with the polymer components by repeatedly spreading a film of the mix onto glass or other suitable surface, with care to avoid air entrapment. The mixture having uniformly dispersed particles can then be pressed into sheets e.g. 0.1 cm thick, or added to a plastic mold to form pellets, and then allowed to cure for about one day at 37° C.

In a preferred embodiment of the invention, the particles are dispersed uniformly within, for release from, a polyethylene-vinyl acetate (EVA) copolymer. A particularly preferred form of EVA copolymer is one having an acetate component of about 40% (referred to simply as EVA-40). Various protocols can be used to construct an EVA-based delivery device, which in general entail the step of mixing the particles in a volumetric ratio of around 20% particles to about 80% polymer. Simple dry mixing of the pellets and polymer can be used, if desired. Alternatively, particle dispersion can be effected either by solvent casting, or by the precipitation method exemplified herein. The solvent casting approach entails mixing appropriate volumes of particles and EVA in a solvent, such as methylene dichloride, and then casting the vigorously agitated suspension in a cold mold. The impregnated polymer solidifies on contact, and is then gradually warmed to room temperature over a period of about two days. A degassing step is desirable, to ensure complete removal of trapped air bubbles.

Once generated, the delivery system, i.e., the particle-laden polymeric matrix may be shaped as appropriate for administration to the patient by the chosen route of administration. Shaping can be achieved by any conventional means, such as by extrusion, injection molding or by melt press. For example, the systems can be made as devices including buccal and oral devices; vaginal and intrauterine devices of cylindrical, bullet, elliptical, circular, bulbuous, loop or any other shape suited for placement in the environments; the devices also include occular devices having any suitable shape and having, in cross-section, a profile that is doubly convex, concavo-convex and the like. For placement on the eye, the delivery device may have a length of from 4 to 10 millimeters, a width of from 1 to 5 millimeters and a thickness of from about 0.1 to 5 millimeters. The delivery devices may also be shaped as implants, for layering on the skin, and for ingestion.

According to a specific embodiment of the invention, the delivery device comprises an EVA matrix and about 20% by volume of uniformly dispersed particles which contain sodium chloride and about 2.5% by weight of a selected therapeutic macromolecule. In a preferred embodiment of the invention, the macromolecule is a protein drug, especially epidermal growth factor (EGF). Delivery devices containing EGF are particularly well suited for delivery by ingestion, to accelerate healing of ulcers, for delivery by application on the eye to heal corneal wounds, and for delivery to surface wounds and burns, to promote healing thereof.

EXAMPLES

In the examples which follow, drug delivery devices are prepared using polyethylene vinyl acetate (EVA-40) as polymeric matrix in monolithic (single layer) form, and using sodium chloride as the electrolyte component of the drug-containing particle. Particles having a size distribution in the 104 $\mu$m to 147 $\mu$m range were used, and were loaded in the EVA polymer, at 20% volumetric loading, in the following manner.

Suspensions of particles in 8 wt % EVA/CH$_2$Cl$_2$ solution were prepared by first wetting the particles in solvent and then adding an appropriate volume of EVA. The mixture was agitated on a rotator mixer for at least 8 hours to ensure complete EVA dissolution. The resulting suspension was quickly poured into an ethanol bath cooled by dry ice to $-75°$ C. and left for one minute. The ribbon-like precipitate containing entrapped salt particles was removed, wiped of excess ethanol, placed onto teflon sheets and put into a $-15°$ C. environment for at least 12 hours. To ensure complete solvent evaporation, the systems were left at room temperature for another 12-24 hours. The EVA/particle systems were melt-pressed to form membranes of 1.3 mm thickness between release liners, and then de-gassed in a vacuum oven heated to roughly 80° C. at 30 psi vacuum until the surface were smooth. Membranes containing protein were degassed at 60° C. Degassed membranes were melt-pressed to 0.9 mm $+/-0.02$ mm. Disks were then cut from the membranes using a 1.9 cm punch.

When viewed under microscope, the particles appeared to be uniformly dispersed. Photographs of cross sections revealed no evidence of polymer skin covering paticles at the surface.

To study the release of drug and salt from the systems, there was used an apparatus which consisted of a nylon mesh bag weighed with a small glass rod, placed into a polypropylene 100 ml tube which sat in a rack in a shaker bath. To obtain a well-stirred environment, the nylon mesh bags were tied by nylon line to a stationary board so that as the rack holding the tubes was displaced horizontally, the nylon mesh bags would move vertically in the tubes.

To observe the maximum effects of osmotic pressure on the release kinetics and fraction releasable, the disks were released into distilled water. At each sample period the solution was replaced with fresh distilled water. Because a burst of salt and macromolecule was anticipated as disks were first placed into the water, the initial sample periods were quite short. At each sampling time the disks were removed from the nylon mesh, and surface water removed by gently patting with tissue, weighed and measured.

To determine the particle fraction releasable by leaching only, without osmotic rupturing, disks were released into solutions of $MgBr_2 \cdot 6H_2O$ of an osmotic strength equivalent to that of a saturated salt solutions at 37° C. Measured aliquots of solution were removed from the release media at specific times. the disks were removed once or twice during the release duration and at the end to be weighed and measured.

The salt released was measured by atomic absorption analysis. Release of bovine serum albumin (BSA) and lysozyme, purchased from a chemical supply house, was analyzed by UV absorption at 280 nm. Release of human epidermal growth factor (EGF), a bacterially produced recombinant product provided by Allelix Biopharmaceuticals Inc. (Mississauga, Canada) was analyzed by HPLC using UV absorbance at 214 nm.

EXAMPLE 1

Release of Bovine Serum Albumin

The effect of the weight fraction of macromolecule admixed with NaCl on the release rate and fraction released was investigated using BSA. The weight fractions of BSA in NaCl were 2.5%, 5%, 10%, 20%. The release profiles for those systems are given in FIG. 1.

With weight fractions of 2.5% and 5%, the BSA release rate in very close to that of NaCl. Monoliths prepared with particles having weight fractions of BSA of 10% and 20% showed different release rates of NaCl and BSA, although the initial fraction released was similar.

At a volumetric loading of 20% and with a particle size distribution of 104–147 $\mu$m, it is likely that not many particles are exposed at the surface, and that the majority of the particles are encapsulated. Particles exposed at the surface will dissolve rapidly, and BSA and NaCl will be release in ratios equal to their particle mass fractions. Therefore, the initial burst phase should be similar for both components. Once the release fraction reaches approximately $Q_D$, the release rate begins to become roughly linear, except for BSA particle mass fractions of 10% and 20%, as expected from earlier analysis. For BSA particle mass fractions of 2.5% and 5%, the release rates of BSA and NaCl are identical, however for the high BSA particle weight fractions the release rate decreases as weight fraction increases.

As a BSA-NaCl particle dissolves, BSA dissolves into the saturated solution of NaCl at the particle-water interface, and the weight fraction of BSA in the solution will be equivalent to its loading in the particle. The solubility of BSA decreases as the ionic strength of the solution increases, however. BSA mass fraction loading less that 0.10 are below the solubility of BSA in the saturated NaCl solution and therefore the BSA concentration in the pumped solution will be equivalent to its loading in the particle. At BSA weight fractions of 10% and 20%, the BSA is loaded above its solubility limit in the NaCl solution surrounding the particle. When capsules containing particles of higher BSA content rupture, the solution in the capsule that is being pumped out will be saturated in NaCl as well as BSA. The higher BSA content results in saturated BSA solution, and excess undissolved BSA. Thus, the release rates of BSA and NaCl will be proportional to their saturation concentrations rather than their weight ratio in the NaCl/BSA particles.

The release of BSA at 10% and 20% particle weight fraction continues long after the NaCl has been totally released. The ratio of the linear release rates of BSA to NaCl are 1.9 and 11.5, for BSA weights of 10% and 20% respectively. Because the release rates from particles of BSA at 10% by weight is approximately twice that of particles of BSA at 5%, it is reasonable to assume that the solubility limit of BSA in saturated NaCl solution is roughly equal to 5% by weight BSA.

EXAMPLE 2

Release of Lysozyme

Figure 2:
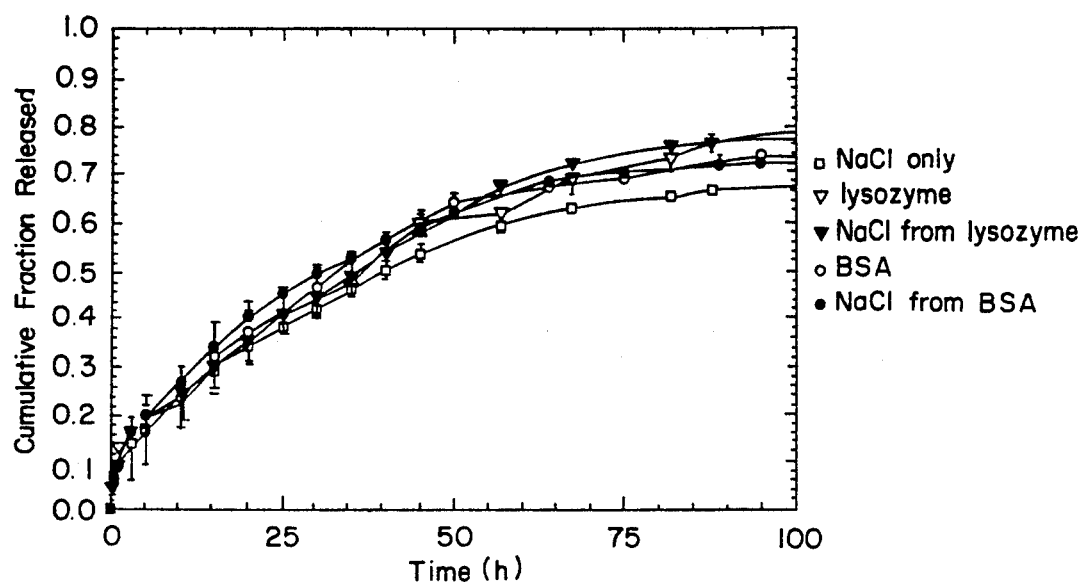
FIG. 2 illustrates in composite form the release profiles of lysozyme and BSA.

Systems were also prepared using NaCl-lysozyme particle having a weight fraction of lysozyme of 25% (particle size 104 $\mu$m to 147 $\mu$m, volumetric loading of 20%). The release profile of NaCl and lysozyme from these systems were compared to the release profiles of NaCl/BSA, as shown in FIG. 2. The release rates are approximately the same for all components released.

EXAMPLE 3

Release of Epidermal Growth Factor (EGF)

EGF is a protein drug having wound healing properties. It has a molecular weight of around 6,200 daltons and is very stable under a variety of conditions. Particles containing 2.5% EGF and 97.5% sodium chloride, by weight, were obtained by colyophilization of an aqueous solution in which EGF and salt were dissolved in appropriate amount by weight. The resulting particles were ground and sieved to recover particles having a size distribution of 104 $\mu$m to 147 $\mu$m, and were then dispersed in EVA-40 polymer as described above, at 20% volumetric loading.

Figure 3:
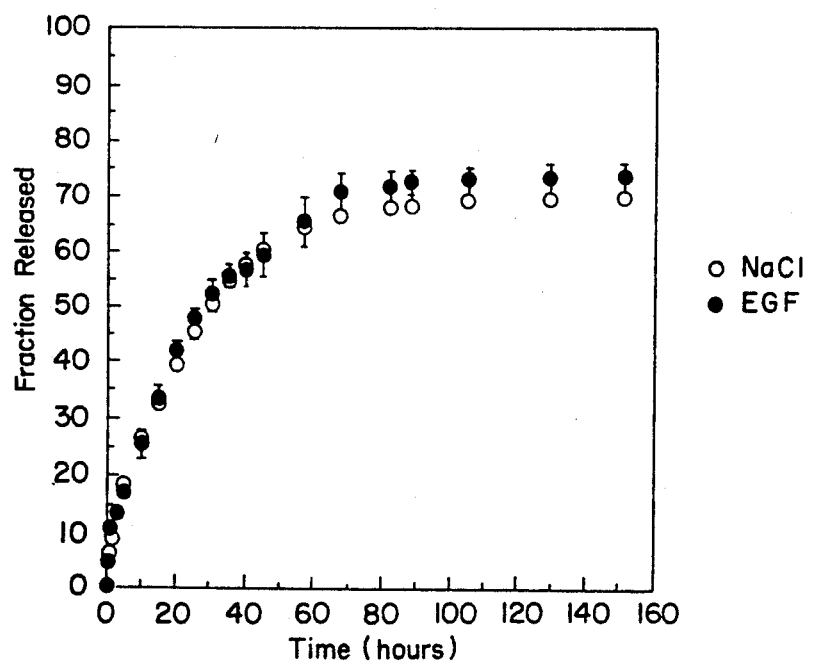
FIG. 3 illustrates the release profile of epidermal growth factor (EGF) from a delivery device of the present invention.

The EGF release profile is provided in FIG. 3. It will be noted that the EGF profile is matched virtually precisely by the salt release profile. Release of EGF from the matrix was sustained, at a constant release rate, for a period of several hours, and at relatively low dose levels.

Thus in accordance with the present invention, release rates of macromolecules can be sustained and controlled by incorporating a small weight fraction of macromolecule into an excipient particle and dispersing these particles uniformly in a polymeric matrix.

We claim:

1. A drug delivery system useful for delivering therapeutic amounts of a drug to a patient in a sustained and controlled fashion, the system comprising a matrix formed of a wettable, polymer and, dispersed uniformly within the polymer, a multiplicity of particles each containing a substantially homogeneous blend of drug and sodium chloride, wherein the amount of drug contained in each of said particles is not greater than about 10% of the particle, by weight.

2. A drug delivery system according to claim 1, wherein the polymer is polyethylene-vinyl acetate copolymer.

3. A drug delivery system according to claim 2, wherein the particles have a size distribution in the range from about 104 μm to about 147 μm.

4. A drug delivery system according to claim 3, wherein the particles dispersed in the polymer are present at a volumetric loading of about 20%.

5. A drug delivery system according to claim 1, wherein the drug contained in the particles is a protein.

6. A drug delivery system according to claim 5, wherein the drug contained in the particles is epidermal growth factor.

7. A drug delivery system useful to deliver epidermal growth factor at low doses to a patient in a sustained and controlled fashion, the system comprising a matrix formed of polyethylenevinyl acetate copolymer and, dispersed uniformly therein at a volumetric loading of about 20%, a multiplicity of particles each comprising a substantially homogeneous blend of sodium chloride and epidermal growth factor, wherein the epidermal growth factor is present in said particles at around 2.5% by weight.

8. A method for delivering a drug to a patient at low dose levels and in a sustained and controlled fashion, which comprises the step of administering to said patient a drug delivery system as defined in claim 5.

9. A method for delivering epidermal growth factor to a patient at low dose levels and in a sustained and controlled fashion, which comprises the step of administering to said patient a drug delivery system as defined in claim 7.

10. A process for preparing a drug delivery system useful to deliver a drug at low dosage levels to a patient in sustained and controlled release fashion, comprising the steps of:

obtaining a substantially homogeneous assemblage of particles, each comprising a substantially homogeneous blend of osmotically active excipient and drug, wherein the drug component of the particles is not more than about 10% by weight: and dispersing said particles uniformly in a wettable polymeric matrix.

11. The process according to claim 10, wherein the particles are dispersed in the matrix at a volumetric loading of about 20%.

12. The process according to claim 11, wherein the excipient is sodium chloride.

13. The process according to claim 12, wherein the matrix is ethylene-vinyl acetate copolymer.

14. A drug delivery system useful for delivering a drug or a combination of drugs at low dosage levels to a patient in a sustained and controlled fashion, the system comprising a matrix formed of a wettable polymer and, dispersed uniformly within the polymer, a multiplicity of particles each comprising a substantially homogeneous blend of drug and osmotically active excipient, the weight ratio of drug to excipient in the particle is less than or equal to the ratio of solubilities of drug to excipient in a saturated salt solution, and wherein the proportion of drug contained in each particle is not greater than about 10% of the particle by weight.

15. A drug delivery system according to claim 14, wherein the particles dispersed in the polymer are present at a volumetric loading in the range from 10% to 30%.

16. A drug delivery system according to claim 14, wherein the drug contained in the particles is a protein.

17. A drug delivery system useful for delivering therapeutic amounts of epidermal growth factor to a patient in a sustained and controlled fashion, the system comprising a matrix formed of a wettable polymer and, dispersed uniformly within the polymer, a plurality of particles each particle of said plurality containing a substantially homogeneous blend of epidermal growth factor and sodium chloride, wherein the amount of drug contained in each said particle is not greater than about 10% of said particle, by weight.

18. A drug delivery system according to claim 17, wherein the particles dispersed in the polymer are present at a volumetric loading in the range of from 10% to 30%.

19. A drug delivery system according to claim 17, wherein the particles have a size distribution in the range from about 104 μm to about 147 μm.

* * * * *